(12) United States Patent
Burgunder et al.

(10) Patent No.: US 9,310,189 B2
(45) Date of Patent: Apr. 12, 2016

(54) METHOD AND SYSTEM FOR THE REMOTE INSPECTION OF A STRUCTURE

(75) Inventors: Samuel Burgunder, Toulouse (FR); Francois Rouyre, Cornebarrieu (FR)

(73) Assignee: AIRBUS OPERATIONS S.A.S., Toulouse (FR)

( * ) Notice: Subject to any disclaimer, the term of this patent is extended or adjusted under 35 U.S.C. 154(b) by 693 days.

(21) Appl. No.: 13/319,842

(22) PCT Filed: May 12, 2010

(86) PCT No.: PCT/FR2010/050935
§ 371 (c)(1),
(2), (4) Date: Feb. 22, 2012

(87) PCT Pub. No.: WO2010/130962
PCT Pub. Date: Nov. 18, 2010

(65) Prior Publication Data
US 2012/0140041 A1  Jun. 7, 2012

(30) Foreign Application Priority Data

May 14, 2009 (FR) ...................... 09 53211

(51) Int. Cl.
*G06K 9/00* (2006.01)
*G01B 11/24* (2006.01)
(Continued)

(52) U.S. Cl.
CPC ............... *G01B 11/24* (2013.01); *G01C 11/02* (2013.01); *G01N 21/9515* (2013.01); *G06T 7/001* (2013.01); *G06T 2207/30164* (2013.01)

(58) Field of Classification Search
None
See application file for complete search history.

(56) References Cited

U.S. PATENT DOCUMENTS

| 4,688,026 A * | 8/1987 | Scribner et al. ............... 235/385 |
| 2002/0172415 A1* | 11/2002 | Asano et al. .................. 382/154 |

(Continued)

FOREIGN PATENT DOCUMENTS

| EP | 0 644 501 | 3/1995 |
| GB | 2 270 155 | 3/1994 |

OTHER PUBLICATIONS

Solomon et al, "Extracting the Shape and Roughness of Specular Lobe Objects Using Four Light Photometric Stereo", Computer Vision and Pattern Recognition, 1992, Proceedings CVPR '92, 1992 IEEE Computer Society Conference on Digital Object Identifier, p. 466-471.*

(Continued)

*Primary Examiner* — Sath V Perungavoor
*Assistant Examiner* — Janese Duley
(74) *Attorney, Agent, or Firm* — Oblon, McClelland, Maier & Neustadt, L.L.P.

(57) ABSTRACT

The invention relates to a method for the remote inspection of a structure, comprising the following operations:
  producing a 3D image of an area of the structure to be inspected,
  superimposing said 3D image with a previously stored digital model of the structure,
  geographically locating the area of the structure to be inspected on the structure model, and
  inspecting the area of the structure to be inspected on the 3D image superimposed with the digital model.
The invention also relates to a system for implementing the method, comprising an imaging device (10) that can be installed in the vicinity of the area of the structure to be inspected (2), and an image-processing device (6) located remotely from the imaging device (10) in order to generate a 3D image from the images captured by the camera (11).

10 Claims, 5 Drawing Sheets

(51) Int. Cl.
*G01C 11/02* (2006.01)
*G01N 21/95* (2006.01)
*G06T 7/00* (2006.01)

(56) References Cited

U.S. PATENT DOCUMENTS

2006/0001839 A1* 1/2006 Beardsley et al. .............. 353/69
2007/0176927 A1 8/2007 Kato et al.
2008/0267487 A1 10/2008 Siri
2009/0002364 A1 1/2009 Witte, II
2010/0235037 A1* 9/2010 Vian et al. ....................... 701/29
2010/0315416 A1* 12/2010 Pretlove et al. ................ 345/419

OTHER PUBLICATIONS

IBM Eng, RC, "Multiple-Image Vision Inspection Process", Sep. 1, 1987, TDB Sep. 1987 p. 1647-1649.*
English translation EP 0644501 A1—Duby et al.*
International Search Report Issued Sep. 10, 2010 in PCT/FR10/050935 Filed May 12, 2010.

\* cited by examiner

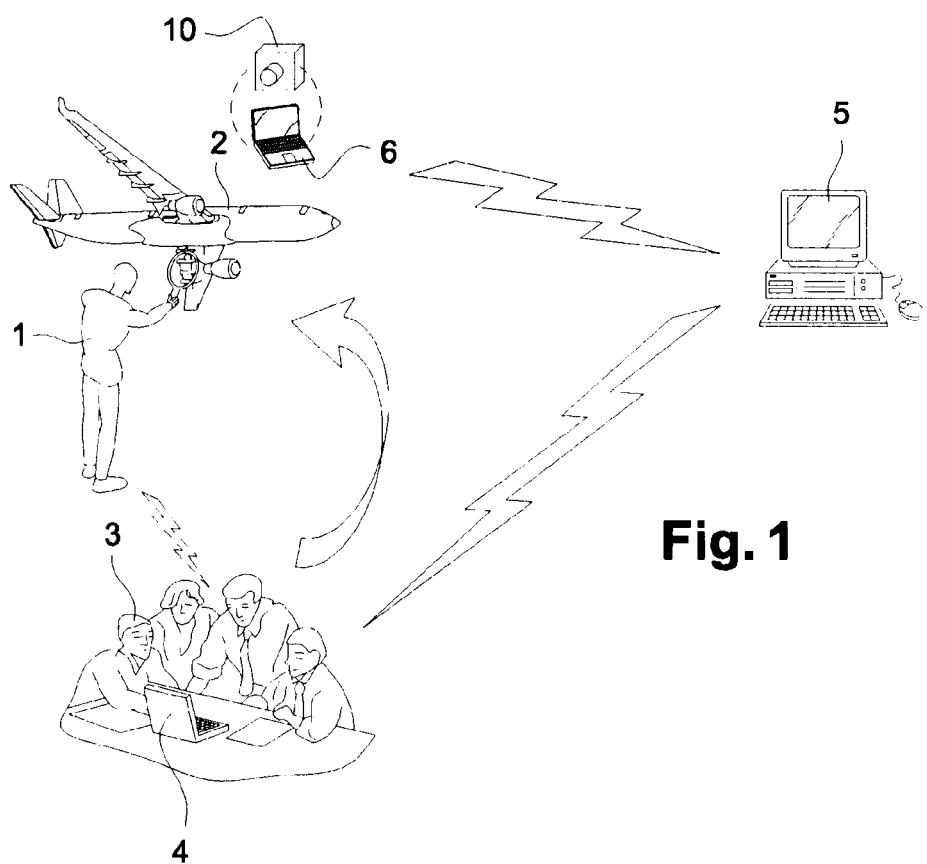
Fig. 1
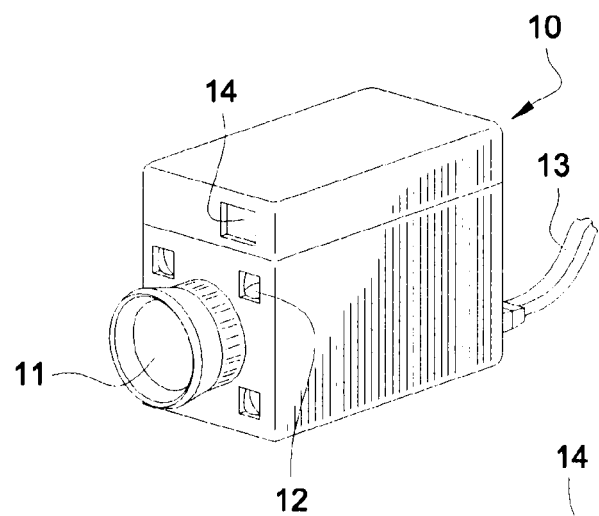
Fig. 2
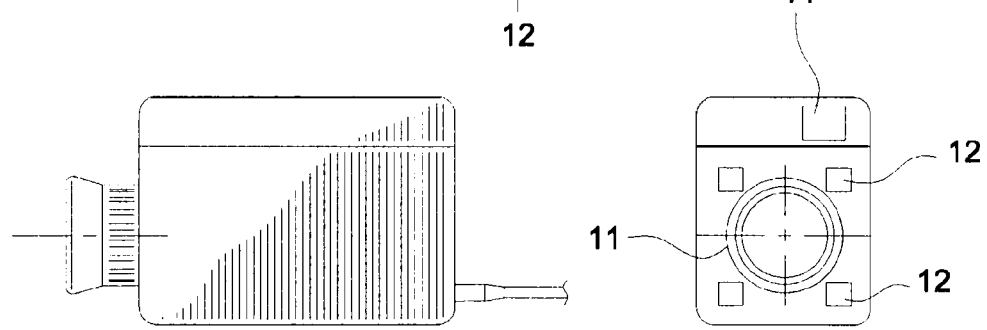

Image 1

Image 2

Image 3

Image 4

3D image

Digital model

METHOD AND SYSTEM FOR THE REMOTE INSPECTION OF A STRUCTURE

FIELD OF THE INVENTION

The invention relates to a method for the remote inspection of a structure, such as an aircraft structure. This method of inspection is used to remotely check the condition of a structure, such as during a maintenance operation. The invention also relates to a system implementing this method.

The invention has applications in the field of computer-assisted monitoring and inspection of structures. In particularly, it has applications in the field of aerospace for the maintenance of aircraft or for the assembly of aircraft structures.

PRIOR ART

Given the level of safety required for an aircraft to be allowed to fly, the maintenance phase is a crucial phase in the life of an aircraft. This maintenance phase requires a detailed inspection of the structure of the aircraft, with repair or replacement of defective parts.

Currently, the maintenance of an aircraft is carried out manually. When the aircraft is on the ground, a maintenance operator boards the aircraft to inspect the areas of the aircraft structure. For this inspection, the maintenance operator is provided a manual that lists the parts of the aircraft structure. This manual is usually presented in paper format or, occasionally, in electronic format. The maintenance operator verifies that the parts he sees are compliant with those listed in the manual. Therefore, the inspection of the structure of the aircraft is done visually by the maintenance operator.

When the maintenance operator identifies a defective part, he takes note of the identification information for the part in order to subsequently replace it with a new part or repair it.

With such a visual inspection, the maintenance operator is alone, on board the aircraft, to inspect the condition of the structure. He is therefore the only person who decides which parts of the structure to replace or repair. The manual is certainly very helpful, but the decision rests solely on the ability of the maintenance operator. It is of course possible for multiple maintenance operators to inspect the entirety of the aircraft, but that increases the maintenance cost. Because maintenance is usually performed by airline companies, the additional cost is effective for each airline company.

Moreover, in an aircraft structure, some parts overlap, or partially overlap, others such that a portion, or the entirety, of a part may be difficult to see. It is then difficult, for the maintenance operator, to make a decision regarding whether to replace or repair such a part.

Also, each part of the structure has an identification number. The identification number is written on the part itself. Also, for the operator to know which part should be replaced or repaired, he must be able to read its reference number. However, if the parts overlap one another, whether fully or partially, it may be difficult, visually, to read the identification number of the relevant part.

DESCRIPTION OF THE INVENTION

The purpose of the invention is precisely to overcome the disadvantages of the techniques described earlier. To this end, the invention provides a method for the inspection of an aircraft structure, assisted by a computer. This method allows the maintenance operator to be assisted, remotely, by an expert. According to this method, the maintenance operator, on board the aircraft, creates a three-dimensional image of the area of the structure to be inspected. This 3D image is superimposed on a digital model of the structure to allow parts to be geographically located. This 3D image superimposed on the digital model can be viewed on a computer, located remotely from the aircraft. An expert can then view, on the computer, the superimposed images in order to assist the operator.

More specifically, the invention relates to a method for the remote inspection of a structure, characterized in that it comprises the following operations:

a) producing a 3D image of an area of the structure to be inspected,
b) superimposing said 3D image with a previously stored digital model of the structure,
c) geographically locating the area of the structure to be inspected on the structure model, and
d) inspecting the area of the structure to be inspected on the 3D image superimposed with the digital model.

The method of the invention can have one or more of the following characteristics:

the 3D image is produced by stereo photometry.
the operation a) for producing a 3D image comprises a successive and intermittent lighting of the area of the structure to be inspected, by light sources each placed at a different location, an image captured at each lighting of the area of the structure to be inspected, and processing of the obtained images in order to produce the 3D image.
the operation a) comprises four captured images of the area of the structure to be inspected, using four different lightings.
the step c) for geographical location comprises a remote operation to point at a part in the area of the structure.
It comprises a preliminary prelocation of the area to be inspected by detecting and reading data contained in chips, each attached to a part of the structure.

The invention also relates to a system for implementing the method for remote inspection of a structure, characterized in that it comprises:

an imaging device (10) that can be installed in the vicinity of the area of the structure to be inspected (2) and comprising multiple light sources (12) arranged around a camera (11), and
an image-processing device (6) connected to the imaging device (10) and capable of generating a 3D image of the area of the structure to be inspected from the images captured by the camera (11), and
a computer (4, 5) far from the structure, said computer or image-processing device being capable of superimposing the 3D image with a digital model of the area of the structure.

This system for remote inspection of a structure can have one or more of the following characteristics:

the light sources are comprised of four LEDs arranged at each corner of one side of the imaging device.
it comprises a computer connected wirelessly to the image-processing device.
the imaging device comprises a device for remotely emitting a laser beam.

BRIEF DESCRIPTION OF THE DRAWINGS

FIG. 1 schematically shows the system of the invention, with the locations of the various elements of the system.

FIG. 2 schematically shows the imaging device of the system of the invention.

DETAILED DESCRIPTION OF THE EMBODIMENTS OF THE INVENTION

Figure 3A:
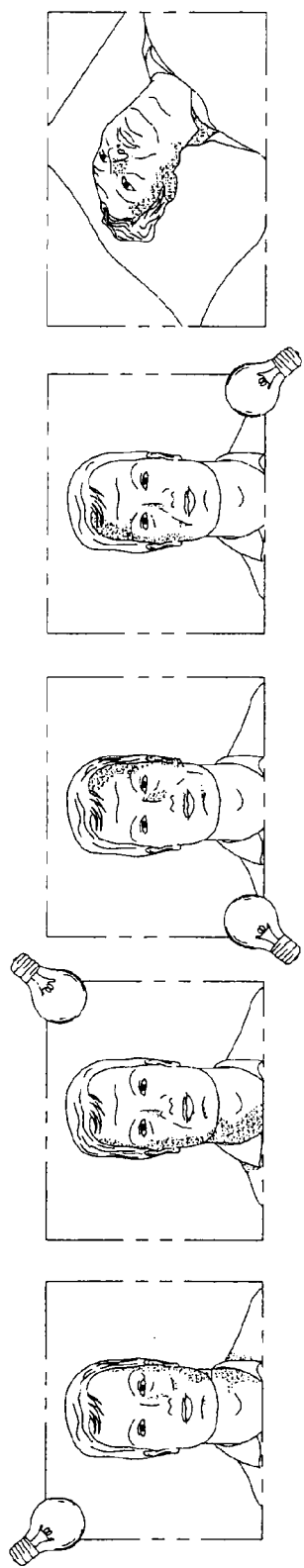
FIGS. 3A and 3B show a series of images produced by the device in FIG. 2.

The invention relates to a method for the inspection of a structure, assisted by a computer. In this method, the structure to be inspected is located at a first location, and the computer is located at a second location that is remote from the first location. The two locations can be a few meters to a few hundred kilometers away from each other. In FIG. 1, an example installation is shown, in which the method of the inspection can be implemented.

In this example, the structure to be inspected is an aircraft structure, inspected for maintenance purposes. An aircraft structure is an element or set of mechanical, electrical, electronic, hydraulic, etc. elements involved in the construction of an aircraft. An aircraft structure can therefore be only a small or large portion of an aircraft or a complete aircraft.

In this FIG. 1, a maintenance operator 1 is shown studying the structure 2 of an aircraft. This maintenance operator 1 is equipped with an imaging device 10. This imaging device 10 is connected to an image-processing device 6 located at the first location, in the aircraft or in the vicinity of the aircraft. This image-processing device 10 can be a computer, such as a laptop computer. This combination of an imaging device 10 and an image-processing device 6, able to be used on site by the operator, allows the operator to inspect the structure of the aircraft autonomously.

This imaging device 10 can also be connected to a computer 5 located in a second location that is remote from the first location. This second location can be, for example, the offices of the airline company that owns the aircraft, the first location being the maintenance workshop of said airline company or an airport parking lot.

The imaging device 10 is connected by means of a traditional connection to the image-processing device 6. In the example in FIG. 1, the imaging device 10 is connected by a wireless connection to the image-processing device 6, itself connected by a wireless connection to the computer 5.

FIG. 1 also shows a third location that is remote from the first and second locations. This third location can be, for example, the offices of the aircraft manufacturer. At this third location is located an expert or group of experts 3 equipped with a computer 4, such as a laptop computer.

The computer 4 at this third location is connected, by a wireless connection, to the image-processing device 6 and to the computer 5.

The expert from the airline company and the expert from the aircraft manufacturer can each receive, on the computer 5 and on the computer 4 respectively, the image obtained after processing by the image-processing device 6. As seen in more detail later, this image is either a superimposed three-dimensional image of the aircraft structure and the digital model corresponding to the aircraft structure or a 3D image of the structure to be inspected (that will be superimposed, on the computer, to the digital model).

Therefore, the operator can autonomously inspect the aircraft structure and decide, on his own, which defective parts to replace. If uncertainty exists, he can request the opinion of an expert from the airline company located at a second location and/or the opinion of an expert from the aircraft manufacture located at a third location.

According to the method of the invention, the inspection of the structure is carried out by comparing actual structure area with the corresponding digital structure area. The expert, from the airline or from the aircraft manufacturer, and the maintenance operator can communicate together, by means of communication that will be mentioned later, in order to exchange their opinions and decide, together, which parts to repair or replace, without the expert needing to travel to the site where the aircraft is parked.

The system to implement this method of inspection of the invention comprises a portable imaging device 10, capable of being moved easily by the maintenance operator. It also comprises an image-processing device 6 and a computer 4 and/or 5. The image-processing device 6 can be a traditional computer, a laptop computer, a tablet PC, or any other means of processing images. It is placed in the vicinity of the structure to be inspected. It can be installed in the aircraft or at a location in the vicinity of the structure. It is connected to the imaging device 10, either by a wired connection or by a wireless connection.

The operator can view the superimposed image of the structure directly on the image-processing device 10. The expert can view the same superimposed image of the structure on a computer 4 and/or 5 far from the structure. The operator may then be assisted, remotely, by an expert. For example, when an aircraft is parked at an airport in a foreign country, the expert from the airline company or the expert from the aircraft manufacturer, located in the offices of the airline company or the aircraft manufacturer, can assist the operator in charge of the maintenance of the aircraft in the foreign country.

The imaging device 10 is a device capable of producing three-dimensional images. An example of a 3D imaging device is shown in FIG. 2. In this example, the imaging device 10 comprises a power cable 13. This cable 13 provides electrical power to the device. It can also transmit information to the image-processing device 6. It should be noted, however, that the electrical power for the imaging device can be supplied by means of a battery mounted inside the device and that the transmission of data to the image-processing device 6 can be carried out by a wireless connection.

The imaging device 10 comprises a 3D camera, depicted in FIG. 2 by its lens. It also comprises light sources 12 located around the lens 11 of the camera. The light sources 12 are evenly distributed around the lens 11. In a preferred embodiment of the invention, there are four light sources 12, each located at a corner of the front of the imaging device. Each light source is produced by means of an electroluminescent diode, or LED, or by means of a set of multiple LEDs. Each LED or set of LEDs has a high enough power to light the area of the structure to be inspected. Lenses can be placed in front of the LEDs to amplify or change the lighting.

In the example in FIG. 2, four LEDs are shown, located on the same front of the imaging device. However, it is possible to install them on the side of the device, so as to make shadows.

These four light sources 12 are intended to intermittently light the area of the structure to be inspected, meaning that each of the light sources lights the same area of the structure to be inspected in sequence. With each lighting by a light source, an image of the area of the structure to be lighted is produced by the camera. The lighting of the structure area is produced in the form of a flash, at very short time intervals. The eye sees only 25 images per second, but cameras can go much further in capturing an image. Because LEDs flash for 1/100 second every 1/25 second, an image is produced every time an LED flashes. Therefore, with a camera that takes 100 images per second, a series of four images can be produced in 1/25 second.

An image of the area of structure is produced with each flash. Multiple images of the same area of the structure, such as four when there are four light sources, are thus produced successively with different lighting for each one. These images, such as four in the example in FIG. 2, are processed in order to produce a three-dimensional, or 3D, image of the structure to be inspected.

This method of producing the 3D image uses a technology called stereo photometry. This technology consists of producing multiple images of a single object, with different lighting, such that each image contains different shadows of the same object. Image processing analyzes the shadow effects on each image and reconstructs a 3D image of the object, with all of its details. The more sources of light there are, the more images there are, and the more accurate the obtained 3D image will be. A stereo photometry image has about 12 levels of gray and makes it possible not only to understand distances but also to order them. This technology, used before now to produce 3D images of individuals, is applied in the invention to a mechanical structure such as an aircraft structure. As part of the invention, it can also be applied to structures other than aircraft structures, such as automobile structures, building structures, public works, etc.

Figure 3B:
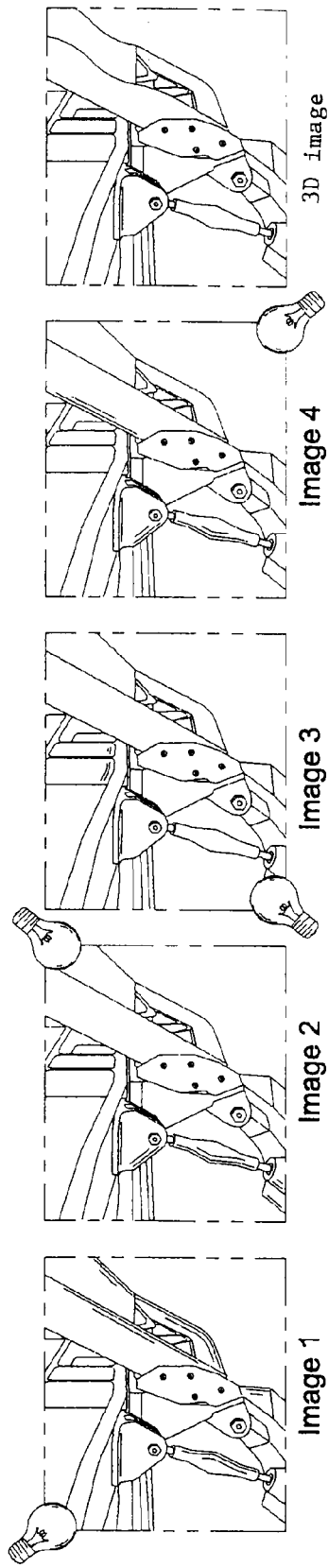

FIG. 3 shows two examples of stereo photometric imaging. Part A of FIG. 3 shows a classic example of using stereo photometry technology, and Part B of FIG. 3 shows an example of using this stereo photometry technology as part of the invention.

In the first series of images, Part A of FIG. 3, an individual is lit by four light sources, and an image is produced with each flash. On these images, the location of the light source used for the relevant image is indicated by a light bulb. We see that, on each image, the light source lights the individual differently, creating different shadows. Processing these shadows makes it possible to obtain the 3D image of the face.

The second series of images, Part B of FIG. 3, shows a method of stereo photometry for an area of an aircraft structure. The area of the structure to be inspected is lit from four different angles, which creates different shadows for each image, with different. The last image shows the 3D image obtained after processing the previous four images.

Figure 4A:
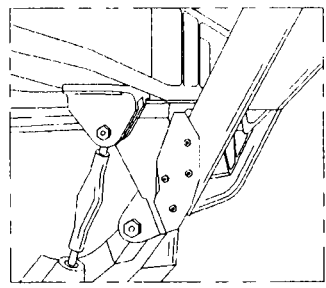
FIGS. 4A, 4B, 4C, and 4D show enlargements of the images in the series of images in FIG. 3.
Figure 4A:
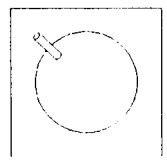
Figure 4B:
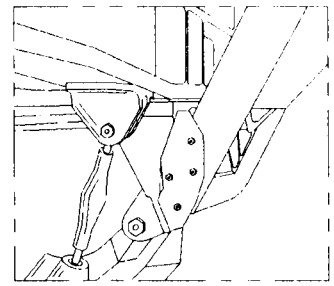
Figure 4B:
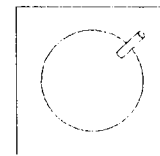
Figure 4C:
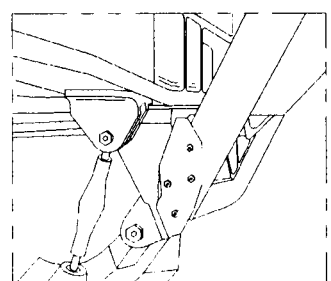
Figure 4C:
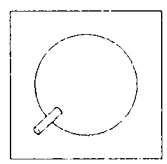
Figure 4D:
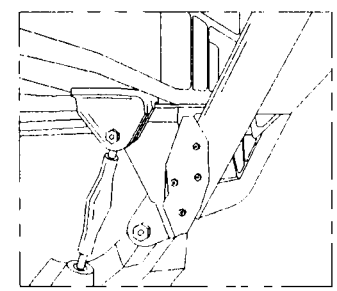
Figure 4D:
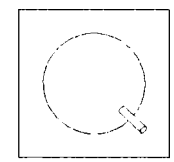

FIG. 4A shows Image 1 from FIG. 3 in more detail, with the location of the light source. Similarly, FIGS. 4B, 4C, and 4D, respectively, show Images 2, 3, and 4 from FIG. 3, with the location of the light source used to produce each of these images.

Figure 5:
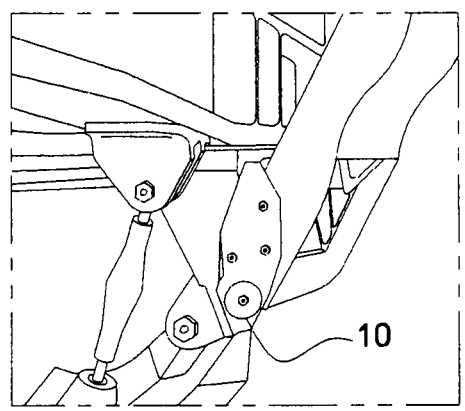
FIG. 5 shows the 3D image obtained from the images in FIGS. 4A, 4B, 4C, and 4D.

FIG. 5 shows the 3D image obtained by processing Images 1, 2, 3, and 4. This image processing uses different grayscales from the four images produced to determine the various heights forming the relief of the 3D image. In the method of the invention, Images 1, 2, 3, and 4 produced by the imaging device 10 are transmitted to the image-processing device 6 that processes them to produce the 3D image.

FIG. 5 shows by a circle and identifies as 10 the location of the imaging device for producing the obtained 3D image. As is understood from the foregoing, the 3D image thus obtained is an actual image of the area of the structure to be inspected. This image corresponds to what the maintenance operator would be able to see if his eyes were at the location 10 of the imaging device.

In the method of the invention, the actual image of the area of the structure to be inspected, the 3D image, is superimposed with a digital image of the same area of the structure. This digital image is a theoretical image of the area of the structure to be inspected. It constitutes the digital model of the structure. Currently, most structures, and specifically most aircraft structures, are designed by use of a computer before they are manufactured. Therefore, a digital format of the structure exists before the structure itself exists. This digital format of the structure is a virtual model of the structure.

Figure 6:
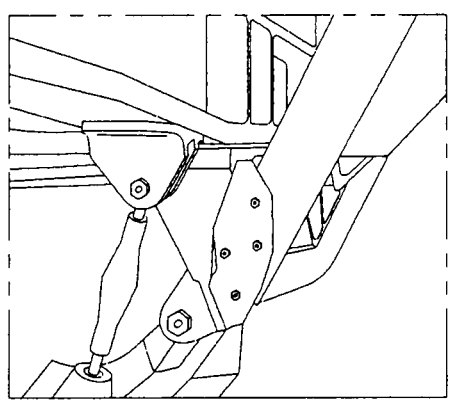
FIG. 6 shows an example of a digital model of an aircraft structure.

FIG. 6 shows an example of the digital model of the area of the aircraft structure corresponding to the area of the structure in the 3D image in FIG. 5.

The invention suggests using this digital model as a theoretical image of the structure. Therefore, according to the invention, the 3D image of the area of structure to be inspected is superimposed with the digital model of this same structure. This superimposing of the 3D image with the digital model allows for geographical location within the area to be inspected, or geographical location within the area within the entire structure.

This superimposing of the 3D image with the model can be carried out in the image-processing device 6 or even in the expert's computer. When it is carried out by the image-processing device 6, the superimposed image is transmitted to the computer 4 and/or the computer 5. When it is carried out by the computer, the 3D image is transmitted to the computer 4 or 5, with the digital model being stored or imported into said computer.

Therefore, the method of the invention consists of producing a 3D image of the area of the structure to be inspected, using images produced by the camera 11, and superimposing this 3D image with the previously stored digital model. The expert can then geographically locate, on the model of the structure, the area of the structure to be inspected, and inspect, on this superimposing of the 3D image with the digital model, said area to be inspected.

Figure 7:
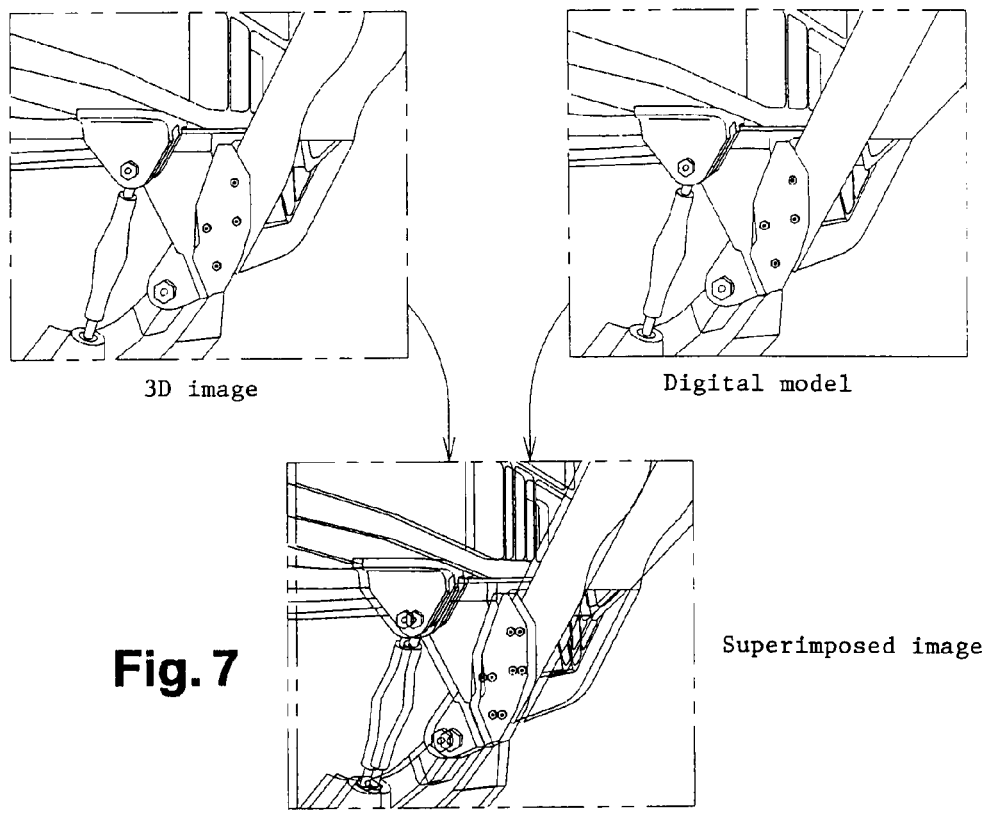
FIG. 7 shows the superimposing of the 3D image with the digital model from the figure of the aircraft structure.

FIG. 7 shows the 3D image of FIG. 5 and the model from FIG. 6. It also shows the superimposed image containing the 3D image of the area to be inspected and the model of this same area. From this superimposed image, the expert can refine and validate the geographical location. The expert then knows where the area to be inspected is located within the structure. In other words, he knows the location of the area photographed by the imaging device. Once the area to be inspected is geographically located, it is possible to examine the condition of the parts in that area. The expert can then examine, using the 3D image, an actual part, meaning a part of the structure that could be damaged, and compare it with the corresponding virtual part. From this comparison, he can determine whether the actual part is defective or whether it is in acceptable condition.

This superimposing of the 3D image with the virtual model of the structure makes it possible to view overlapping parts, meaning parts that are located in front of one another, as well as parts located beneath the trim of the structure, despite the naked eye being able to see only the trim itself. It also allows the expert to view what is between overlapping parts. It also allows the expert to superimpose, using the virtual model, the repairs that have already been recorded in the area.

During the inspection of the area of the structure, the expert can communicate with the maintenance operator through a traditional communication means. He can communicate through the computer, such as over an Internet or intranet connection, by phone, or by any known means of communication. By this communication, he can request images of another area of the structure, he can request for a measurement to be retaken, he can exchange opinions with the operator, or he can tell the maintenance operator to replace or repair a part.

To communicate with the operator, such as to tell him about a damaged part, the expert can use a laser beam as a pointer. This laser beam is generated by a remote controlled laser emitting device, shown in FIG. 2 by reference 14. This laser beam 14 serves as a pointer to identify a specific item in the area of the structure to be inspected. This pointer can be in the form of an X, a circle, or square, or any other shape to indicate an item in the area to be inspected.

Figure 8:
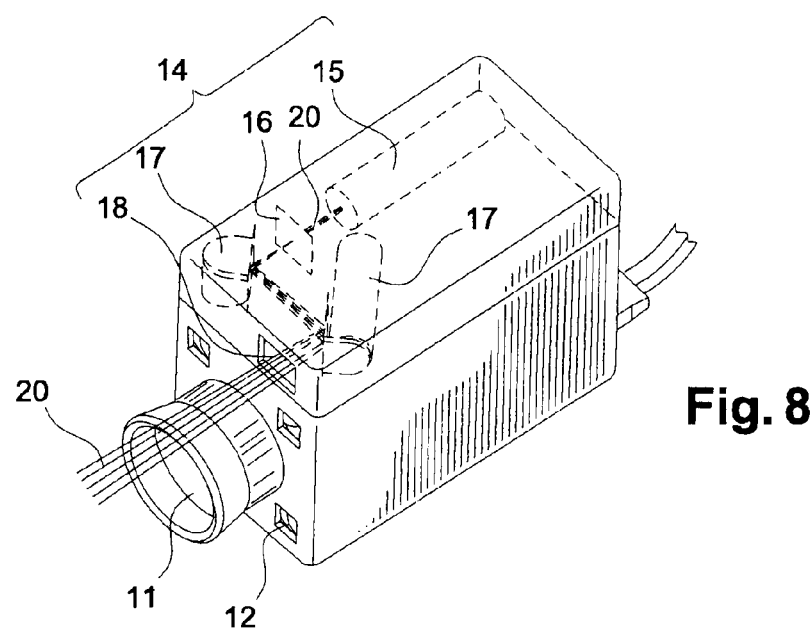
FIG. 8 shows the imaging device equipped with a device for issuing a laser beam.

FIG. 8 shows an example of an imaging device according to the invention, equipped with a device for issuing a laser beam 14. This emitting device 14 comprises a laser generator 15 emitting a laser beam 20. It also comprises a prism 16 constituting the shape of the pointer. This prism can have the shape of an X so that the laser pointer is in the shape of an X. This prism can be interchangeable so that different pointer shapes can be obtained.

The laser beam obtained from the prism 16 can be directed horizontally and/or vertically. This direction is obtained by reflecting the laser beam onto mirrors or prisms moved by means of a horizontal motor 17 and a vertical motor 19. The laser beam 20, once directed, is emitted through an output window 18.

The direction of the laser beam 20 is remote controlled from the computer 4 or 5. In other words, the laser beam is remote controlled by the expert. It can be remote controlled using the mouse connected to the computer on which the expert is viewing the area of the structure. This way, the expert can tell the operator exactly which item needs to be repaired or replaced. This remote control of the laser pointer reduces the risk of error due to a misunderstanding between the operator and the expert.

The laser pointer can also constitute a fixed target on a part of the virtual model, thereby eliminating any parasitic movement of the imaging device. This method of fixing the laser pointer makes it possible to identify a virtual point on the airplane corresponding to a virtual point on the model. Once the laser pointer is fixed, it is possible to rotate the camera around a part connected to the observation area. For example, it is possible to visually rotate around a screw to find the nut that fits the screw from the other side of a wall or part.

Moreover, we know that it is increasingly more common to install chips on each part of a structure in order to quickly determine the characteristics and features of the part. These RFID chips contain information about their shape, location, etc. The method of the invention may comprise a preliminary prelocation step in the area of the structure to be inspected. For this, the imaging device of the system of the invention includes a chip reader capable of reading the data recorded on the chip for the part from which it will produce images. This prelocation has the advantage of reducing the data processing carried out by the computer to geographically located the area within the structure to be inspected. With such a method, the location of the part is determined immediately when the imaging device approaches the location of the chip. The geographical location processing is carried out immediately on the area whose location was provided by the chip.

The invention has been described with an example of aircraft maintenance. It can also be applied to the installation of parts forming an airplane structure, such as to verify the quality of the installation after assembly and to see whether the installed structure correctly matches the model.

It can also be used to analyze or preview a range of installations before application on an airplane by overlaying a virtual image over an actual image.

The invention can also be used in flight, by the crew, in the event of damage to the apparatus or embedded systems. It can also be used in flight to film a specific event live as it occurs in the aircraft, with the produced images being used as evidence of what took place.

The system of the invention described herein provides maintenance assistance and remote decision-making. It can also serve as a link between a maintenance operator on the aircraft and the maintenance office of the airline company.

The system of the invention can also allow automatic identification of the structure. For example, when the connection is established, a series of bits can identify the structure in question and the aircraft for which it was assigned.

This system can therefore provide technical support and maintenance that comes with the aircraft.

The method described above uses a video camera. A thermal imaging camera could be added to the imaging device to allow inspection of the ailerons. A photogrammetric camera could also be added to provide sizing information.

The invention claimed is:

1. A method for the remote inspection of a structure, comprising the following operations:
    a) producing a 3D image of an area of the structure to be inspected using an imaging device operated by a user and that is installed in a vicinity of the area of the structure to be inspected;
    b) superimposing said 3D image with a previously stored digital model of the structure, the superimposing of the 3D image with the previously stored digital model is performed on an image processing device positioned in the vicinity of the area of the structure to be inspected;
    c) geographically locating the area of the structure to be inspected on the 3D image superimposed with the digital model; and
    d) inspecting the area of the structure to be inspected on the 3D image superimposed with the digital model.

2. The method according to claim 1, wherein the 3D image is produced by stereo photometry.

3. The method according to claim 2, wherein the operation a) of producing a 3D image comprises:
    a successive and intermittent lighting of the area of the structure to be inspected, by light sources each placed at a different location,
    an image captured at each lighting of the area of the structure to be inspected, and
    processing of the obtained images in order to produce the 3D image.

4. The method according to claim 3, wherein the operation a) comprises four captured images of the area of the structure to be inspected (image1, image2, image3, and image4), using four different lightings.

5. The method according to any one of claims 1 to 4, wherein the geographical location step c) comprises an operation for using remote control to point to a part of the structure area.

6. The method according to any one of claims 1 to 4 wherein it comprises a preliminary prelocation of the area to be inspected by detecting and reading data contained in chips, each attached to a part of the structure.

7. A system for implementing the method for remote inspection of a structure according to any one of claims 1 to 4, comprising:
- a camera as the imaging device that includes multiple light sources arranged around the camera, and
- an image-processing device connected to the imaging device and capable of generating a 3D image of the area of the structure to be inspected from the images captured by the camera, and
- a computer far from the structure, said computer or image-processing device being capable of superimposing the 3D image with a digital model of the area of the structure.

8. The system according to claim 7, wherein the light sources are comprised of four LEDs arranged at each corner of one side of the imaging device.

9. The system according to claim 7, further comprising a computer connected by a wireless connection to the image-processing device.

10. The system according to claim 7, wherein the imaging device comprises a remote controlled laser emitting device.

\* \* \* \* \*